(12) United States Patent
Kimura (10) Patent No.: US 7,157,727 B2
(45) Date of Patent: Jan. 2, 2007

(54) OPTICAL DETECTOR ABLE TO SENSE THE PRESENCE OF A CONTAINER AND CONTENT THEREIN, AND CONTAINER AND PRINTER USING THE SAME

(75) Inventor: Hitotoshi Kimura, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 11/111,430

(22) Filed: Apr. 21, 2005

(65) Prior Publication Data

US 2005/0236590 A1    Oct. 27, 2005

(30) Foreign Application Priority Data

Apr. 21, 2004   (JP)   ............... P2004-125450

(51) Int. Cl.
*G01B 5/28*    (2006.01)
*B41J 2/195*   (2006.01)

(52) U.S. Cl. .............. 250/576; 250/573; 250/574; 250/577; 250/227.25; 73/290 R; 73/293; 347/7; 347/86

(58) Field of Classification Search ........ 250/573–577, 250/900, 227.25; 347/6, 7, 86; 73/290 R, 73/290 B, 293; 340/618, 619; 116/227
See application file for complete search history.

(56) References Cited

U.S. PATENT DOCUMENTS 4,878,383 A * 11/1989 Wiegand et al. ............. 73/293
6,137,503 A   10/2000 Hashimoto et al.
6,361,136 B1 * 3/2002 Watanabe et al. ............. 347/7
6,626,510 B1 * 9/2003 Maeda ......................... 347/7
6,705,715 B1 * 3/2004 Morita et al. ............... 347/87
7,040,728 B1 * 5/2006 Merz et al. .................. 347/7
2004/0232364 A1 * 11/2004 Omatoi ....................... 250/577

FOREIGN PATENT DOCUMENTS

JP    07-164626 A    6/1995
JP    10-230616 A    9/1998

* cited by examiner

*Primary Examiner*—Stephone B. Allen
*Assistant Examiner*—Davienne Monbleau
(74) *Attorney, Agent, or Firm*—Stroock, & Stroock & Lavan LLP (57) ABSTRACT

A content detecting apparatus uses a signal from a light-receiving part receiving light projected from a light emitting part to detect ink in an ink cartridge. The light-emitting part and the light-receiving part are arranged with differing optical axes. The ink cartridge has reflecting parts for reflecting projected light from the light-emitting part so the projected light reaches the light-receiving part when remaining content is present when the ink cartridge is properly set and with an inclined interface located in a path along which projected light from the light-emitting part reaches the light-receiving part, for switching between permeation and reflection according to the presence and/or absence of remaining content. The inclined interface is permeated along the path with projected light form the light-emitting part when remaining content is present and reflects projected light from the light-emitting part out of the path when remaining content is absent.

10 Claims, 7 Drawing Sheets

OPTICAL DETECTOR ABLE TO SENSE THE PRESENCE OF A CONTAINER AND CONTENT THEREIN, AND CONTAINER AND PRINTER USING THE SAME

BACKGROUND OF THE INVENTION

The present invention relates to a content detecting apparatus preferably used for detecting ink remaining in an ink-jet printer, a container used for the content detecting apparatus and an ink-jet printer in which the container is used as an ink cartridge.

Up to now, there has been a detecting apparatus proposed as a technique for detecting presence and/or absence of ink remaining in a ink cartridge, the detecting apparatus being arranged that a prism having two inclined interfaces for reflecting twice light projected from a light-emitting part to let the projected light reach a light-receiving part be provided on a bottom of the ink cartridge formed from a material of a refractive index almost equal to that of the ink, which is a content, and that the inclined interfaces of the prism function as a reflecting surface to let the projected light reach the light-receiving part when the remaining ink is absent while the inclined interfaces function as a light permeable surfaces to let the projected light not reach the light-receiving part when the remaining ink is present (refer to JP-A-1995-164626, for example).

Such a detecting apparatus, however, has a problem such that it is impossible to make distinction for judgment between a signal at the light-receiving part in the case of absence of a cartridge (a signal indicating no received light) and a signal at the light-receiving part in the case of absence of remaining ink (a signal indicating no received light) since the both signals are same.

In view of the above, there has been a detecting apparatus proposed in which a prism for detecting presence and/or absence of the ink cartridge is provided on the bottom of the cartridge in addition to the above-mentioned prism for detecting remaining ink to relatively move the same light-receiving/emitting parts between the both prisms so that both of the detection of presence and/or absence of remaining ink and the detection of presence and/or absence of a cartridge can be carried out (refer to JP-A-1998-230616, for example).

The detecting apparatus disclosed in Patent Reference 2, however, has a problem that a structure and/or an operation thereof are complicated since a prism for detecting presence and/or absence of a cartridge should be provided separately from a prism for detecting presence and/or absence of remaining ink in addition to a requirement of relative movement of light-receiving/emitting parts between the both prisms.

SUMMARY OF THE INVENTION

An object of the invention thus relates to solving the above problems. The object of the invention is to provide a content detecting apparatus capable of detecting presence and/or absence of loaded container and remaining content only at one place, a container used for the content detecting apparatus and an ink-jet printer using the container as an ink cartridge.

The above object of the invention can be achieved by a content detecting apparatus for detecting presence and/or absence of a remaining content in a container by means of a signal from a light-receiving part receiving light projected from a light-emitting part, wherein the light-emitting part for emitting light toward the container set in a container setting part and the light-receiving part for receiving the light projected from the light-emitting part are arranged so that optical axes thereof would not accord, the container is provided with a reflecting surface for reflecting the light projected from the light-emitting part to let the projected light reach the light-receiving part when the remaining container is present and with an inclined interface, which is located in a path through which the light projected from the light-emitting part reaches the light-receiving part, for switching a function between permeation and reflection in accordance with presence and/or absence of the remaining container under a condition that the container is properly set in the container setting part, and the inclined interface reflects along the path the light projected from the light-emitting part when the remaining content is present while the inclined interface reflects the light projected from the light-emitting part in a direction out of the path when the remaining content is absent.

In accordance with such a structure, the light projected from the light-emitting part reaches the light-receiving part when the container can be properly set in the container setting part and an amount of ink remaining in the container is at a predetermined level or more. That is to say, when the remaining content is present (an amount of the remaining content is at a predetermined level or more), the light projected from the light-emitting part is reflected on the reflecting surface to reach the light-receiving part since the inclined interface provided in the container functions as a permeable surface so that the projected light from the light-emitting part would permeate the inclined interface. Accordingly, when the light-emitting part emits light and the light-receiving part receives the emitted light, it can be judged that there is a container as well as the remaining content.

On the other hand, the projected light from the light-emitting part does not reach the light-receiving part when an amount of the remaining content is less than the predetermined level even in the case that the container is properly set in the container setting part. That is to say, when the remaining content is absent (the remaining content is less than the predetermined level), the inclined interface provided in the container functions as a reflecting surface to reflect the projected light from the light-emitting part in a direction out of an optical path, which is in the case of presence of the content, so that the projected light from the light-emitting part does not reach the light-receiving part.

Further, optical axes of the light-emitting part and the light-receiving part do not accord when the container is not set in the container setting part. Accordingly, even when the light-emitting part emits light, the projected light does not reach the light-receiving part.

Similarly to the above, in the case that the container is not properly set in the container setting part, the reflecting surface of the container also does not effectively function even when the remaining content is present, so that the projected light from the light-emitting part does not reach the light-receiving part. Accordingly, the case that projected light does not reach the light-receiving part even when the light-emitting part emits the light can be judged to be a case that the container is not properly set or a case that there is no remaining content even when the container is properly set.

That is to say, it can be judged that the content can be used (the content is present) when the light-receiving part outputs a light-receiving signal with the light-emitting part emitting light while the content cannot be used (the content is absent) when the light-receiving part does not output a light-receiving signal.

It is preferable in the content detecting apparatus that the reflecting surface includes a first reflecting surface for reflecting the light projected from the light-emitting part and a second reflecting part for reflecting the reflected light toward the light-receiving part and that the inclined interface is provided between the first reflecting surface and the second reflecting surface.

In accordance with such a structure, using two reflecting surfaces to let the projected light from the light-emitting part reach the light-receiving part allows the light-emitting part and the light-receiving part to be provided on the same side with optical axes thereof being parallel, so that the light-receiving and light-emitting parts can be made compact.

Further, it is preferable in the content detecting apparatus that a direction of reflection of light by means of the inclined interface in the case of absence of the remaining content is set on the inner side of the container.

In accordance with such a structure, the apparatus can be preferably used in the case that the light is not desired to be reflected to the outside of the container.

Moreover, it is preferable in the content detecting apparatus that a direction of reflection of light by means of the inclined interface in the case of absence of the remaining content is set on the outer side of the container.

In accordance with such a structure, the apparatus can be preferably used in the case that the light is not desired to be reflected to the inner side of the container.

In addition to the above, it is preferable in the content detecting apparatus that a container wall surface, which is permeated with light subsequently to the inclined interface, is formed parallel to the inclined interface.

In accordance with such a structure, the thickness of the container at a part where the inclined interface is provided can be made thin. The permeable wall surface is originally preferable to be provided vertically to a light permeable direction (considering adjustment of location of the light-emitting part and the light-receiving part) in order to avoid refraction of light in permeating the container wall surface. This, however, causes an unnecessary thick part, which is not preferable in forming the container from resin.

It is further preferable in the content detecting apparatus that the content is liquid. This allows the apparatus to be effectively applied to detection of presence and/or absence of remaining liquid.

Furthermore, it is preferable in the content detecting apparatus that a space for preventing wrong detection of the content due to a meniscus is secured in the inner side of the container adjacent to the inclined interface.

In accordance with such a structure, securing a space for preventing a detection error due to a meniscus adjacently to the inclined interface allows probability of the detection error due to a meniscus to be removed. That is to say, when a space adjacent to the inclined interface is small, a meniscus operation is likely to cause liquid to be adhered to the inclined interface although the amount of the liquid, which is the content, is little, so that the inclined interface does not function as a reflecting surface. This causes a probability of the detection error. The above structure can prevent such a probability.

The above object of the invention can be achieved by a container, which is loaded in a container setting part provided with a light-emitting part and a light-receiving part so that the optical axes of the light-emitting part and the light-receiving part would not accord and in which presence and/or absence of a remaining content is detected, the container comprising: under a condition that the container is properly set in the container setting part, a reflecting surface for reflecting the light projected from the light-emitting part to let the projected light reach the light-receiving part when the remaining container is present; and an inclined interface, which is located in a path through which the light projected from the light-emitting part reaches the light-receiving part, for switching a function between permeation and reflection in accordance with presence and/or absence of the remaining container, the container wherein the inclined interface is arranged to be permeated along the path with the light projected from the light-emitting part when the remaining content is present and to reflect the light projected from the light-emitting part in a direction out of the path when the remaining content is absent.

In accordance with such a structure, applying the container to the above-mentioned content detecting apparatus allows the above-mentioned effect to be obtained.

It is preferable in the container that the container is in a mode of an ink cartridge capable of being loaded in an ink-jet printer, which houses ink as the content and uses the ink as a printing material.

In accordance with such a structure, the invention can be preferably applied to an ink cartridge.

Further, the object of the invention can be achieved by an ink-jet printer comprising: holding means for detachably holding a container; detecting means including a light-emitting part and a light-receiving part for radiating light and receiving reflected light to or from the reflecting surface and the inclined interface provided in the container; and driving means for relatively moving the holding means and the detecting means.

In accordance with such a structure, the invention can be preferably applied to an ink-jet printer.

In the content detecting apparatus in accordance with the invention, it can be judged that the content can be used when the light-receiving part outputs a light-receiving signal with the light-emitting part emitting light while the content cannot be used when the light-receiving part does not output a light-receiving signal.

Therefore, providing one combination of the inclined interface and the reflecting surface and only once performing positioning between the light-emitting and light-receiving parts and the container allow presence and/or absence of the container and presence and/or absence of the remaining content to be simultaneously judged.

Accordingly, presence and/or absence of the loaded container and presence and/or absence of the content remaining in the container can be detected only at one place, so that there is no need to relatively move the light-receiving and light-emitting parts. This allows a structure and/or an operation of the detecting apparatus to be simplified.

The present disclosure relates to the subject matter contained in Japanese patent application No. 2004-125450 (filed on Apr. 21, 2004), which is expressly incorporated herein by reference in its entirety.

BRIEF DESCRIPTION OF THE DRAWINGS

FIG. 1 is a schematically sectional view of a structure of an apparatus for detecting the amount of remaining ink in a first embodiment of the invention, in which FIG. 1A is an illustration showing a condition that there is ink remaining in the apparatus, FIG. 1B is an illustration showing a condition that the remaining ink is absent in the apparatus, and FIG. 1C is an illustration showing a condition that there is no cartridge in the apparatus.

FIG. 2 is a perspective view of a part of a bottom of a cartridge, in which FIG. 2A is An upper perspective view of the part of a bottom of a cartridge, and FIG. 2B is a lower perspective view of the part of a bottom of a cartridge.

FIG. 3 is an illustration showing a whole structure of the cartridge, in which FIG. 3A is a lower perspective view of the cartridge, and FIG. 3B is a vertically sectional view of the cartridge.

FIG. 7 is a schematically sectional view of a structure of an apparatus for detecting the amount of remaining ink in the fifth embodiment of the invention, in which FIG. 7A is an illustration showing condition that remaining ink is present in the apparatus, FIG. 7B is an illustration showing a condition that the remaining ink is absent in the apparatus, and FIG. 7C is an illustration showing a condition that there is no cartridge in the apparatus.

DESCRIPTION OF THE PREFERRED EMBODIMENT

Embodiments of the invention will be described in detail hereinafter on the basis of the attached drawings.

<Embodiment 1>

Figure 1:
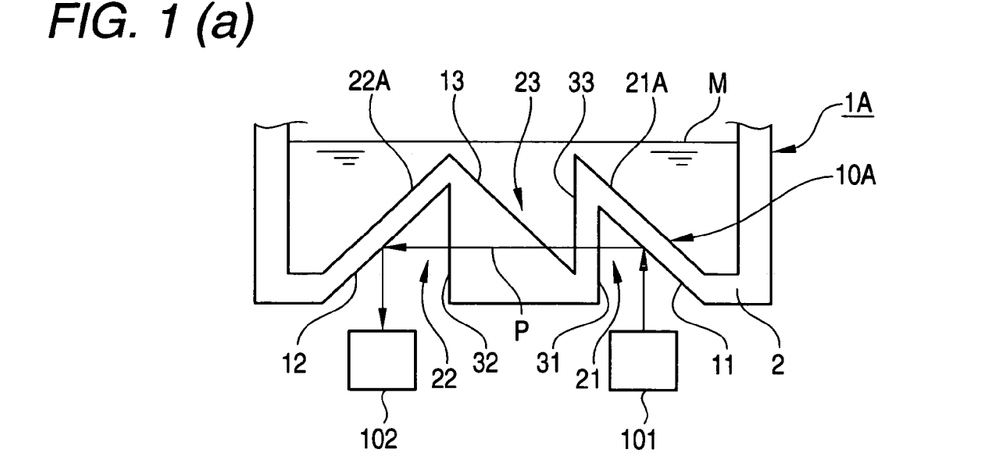
Figure 2:
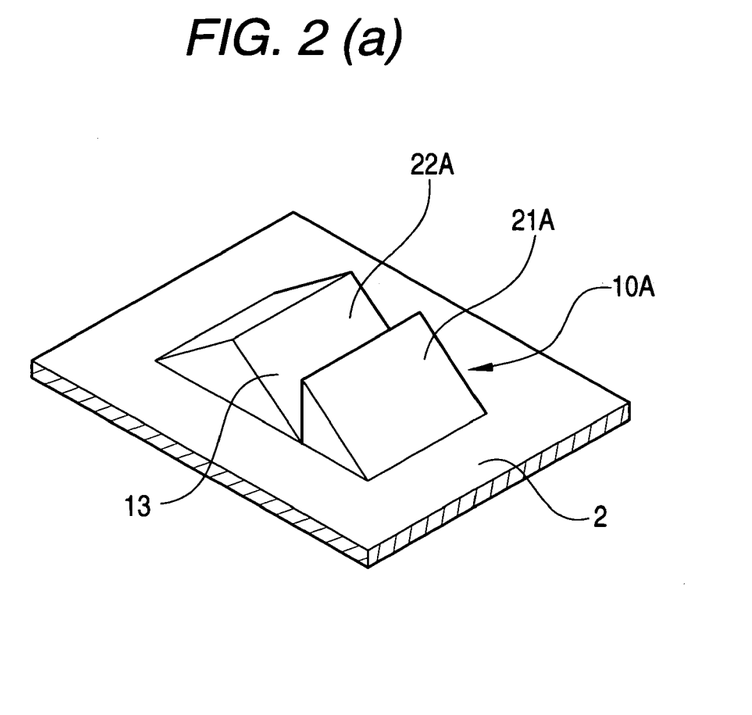
Figure 3:
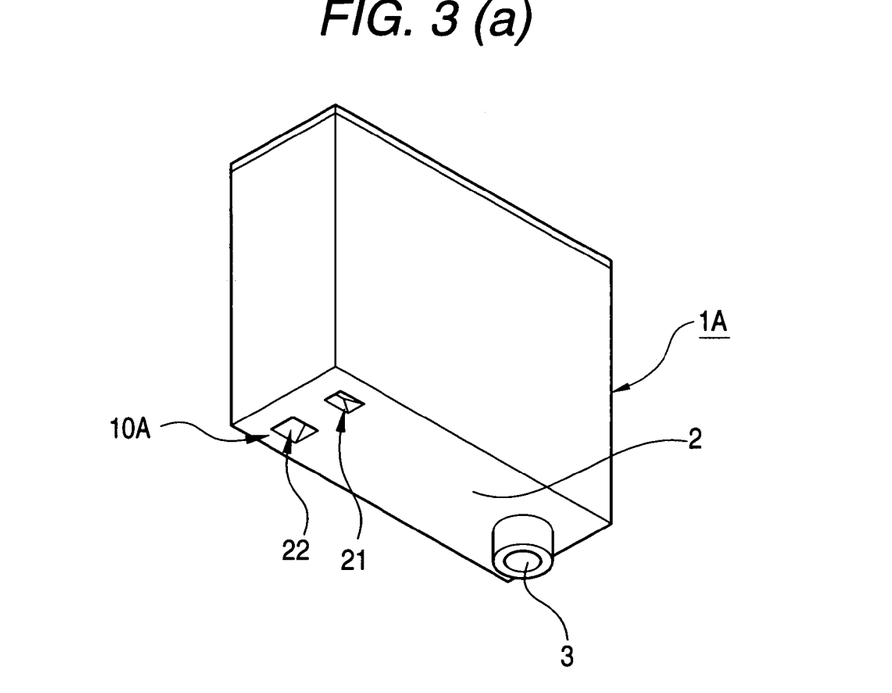

FIG. 1 is a schematically sectional view of a structure of an apparatus for detecting the amount of remaining ink in the first embodiment of the invention. FIG. 1A shows a condition that there is ink remaining in the apparatus. FIG. 1B shows a condition that the remaining ink is absent in the apparatus. FIG. 1C shows a condition that there is no cartridge in the apparatus. FIG. 2 is a perspective view of a part of a bottom of a cartridge. FIG. 2A is an upper perspective view of the above. FIG. 2B is a lower perspective view of the above. FIG. 3 shows a whole structure of the cartridge. FIG. 3A is a lower perspective view of the cartridge. FIG. 3B is a vertically sectional view of the cartridge.

An apparatus for detecting the amount of remaining ink in Embodiment 1 is a content detecting apparatus for detecting presence and/or absence of ink M remaining in an ink cartridge 1A and presence and/or absence of the ink cartridge 1A, as shown in FIG. 1.

The ink cartridge 1A is freely attachable to a cartridge setting part (a container setting part) of a carriage 211 of a later-mentioned ink-jet printer 200, for example (refer to FIG. 8).

Figure 8:
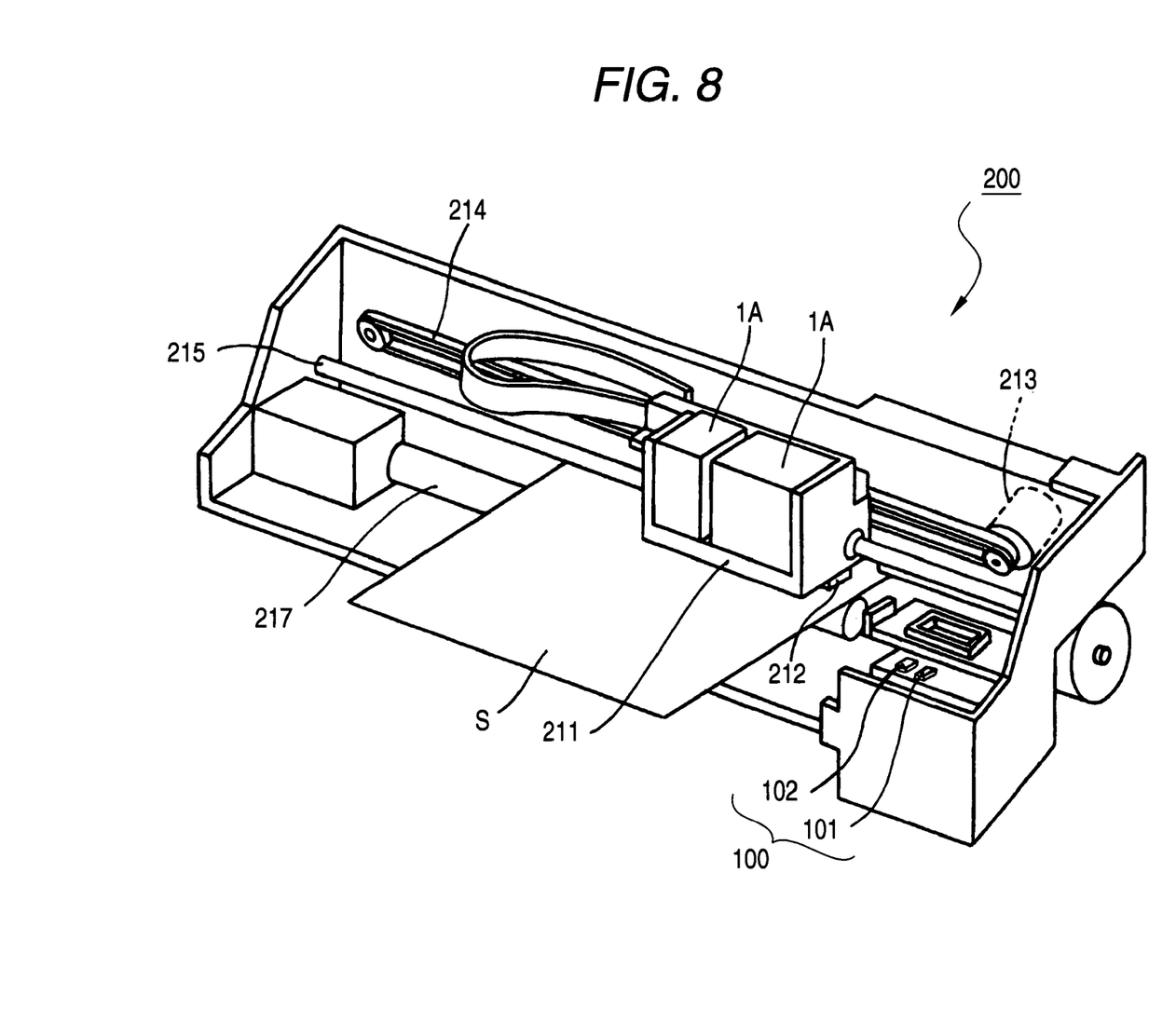
FIG. 8 is a schematic illustration of a structure of an ink-jet printer on which the apparatus for detecting the amount of remaining ink in an embodiment of the invention is mounted.

As shown in FIGS. 3 and 8, the ink cartridge 1A is provided on a bottom wall part 2 thereof with an ink introducing part 3. The ink cartridge 1A supplies an ink-jet head 212 with the ink M while it is attached to the cartridge setting part.

A light-emitting part 101 and a light-receiving part 102 are arranged that light be projected from the light-emitting part 101 toward the bottom wall part 2 of the ink cartridge 1A set in the cartridge setting part to be received at the light-receiving part 102 so that presence and/or absence of the ink M remaining in the ink cartridge 1A and presence and/or absence of the ink cartridge 1A would be detected.

The light-emitting part 101 and the light-receiving part 102 are also arranged so that their optical axes would not accord in order to prevent the projected light from the light-emitting part 101 from being directly incident on the light-receiving part 102. Especially in Embodiment 1, the light-emitting part 101 and the light-receiving part 102 are arranged so that their optical axes would be parallel each other in the same direction (upward in the drawing).

In FIGS. 1A and 1B, the ink cartridge 1A is assumed to be properly set in the cartridge setting part of the carriage 211. In the bottom wall part 2 of the ink cartridge 1A, formed is a remaining amount detecting part 10A. At least the bottom wall part 2 of the ink cartridge 1A in which the remaining amount detecting part 10A is formed is formed from an optically permeable material having a refractive index almost equal to that of the ink M.

As shown in FIG. 1A, the remaining amount detecting part 10A is provided with first and second reflecting surfaces 11 and 12 for reflecting twice the projected light from the light-emitting part 101 to let the projected light reach the light-receiving part 102 when the remaining ink is present and with an inclined interface 13 located in a path P along which the projected light from the light-emitting part 101 reaches the light-receiving part 102 (a path shown by an arrow in the drawings), the inclined interface 13 switching its function between permeation and reflection in accordance with presence and/or absence of the remaining ink.

The first and second reflecting surfaces 11 and 12 are formed from concaves 21 and 22 in the shape of a triangle in section, the concaves 21 and 22 being provided in the bottom wall part 2 of the ink cartridge 1A from the bottom side of the bottom wall part 2, as shown in FIG. 2. The inclined interface 13 is formed from a concave 23 in the shape of a triangle in section, the concave 23 being provided in the bottom wall part 2 from the inner side (the upper side) of the cartridge.

The inner concave 23, which forms the inclined interface 13, is formed between convexes 21A and 22A, which are in the shape of a mountain toward the inner side of the outer concaves 21 and 22. The inclined interface 13 is thus located between the first and second reflecting surfaces 11 and 19.

The first and second reflecting surfaces 11 and 12 and the inclined interface 13 are respectively formed from an inclined surface at a 45° angle with an emitting optical axis of the light-emitting part 101.

The first and second reflecting surfaces 11 and 12 are arranged so as to have a locational relation therebetween such that the first reflecting surface 11 changes a direction of the projected light from the light-emitting part 101 (shown by an arrow in the drawings) at an angle of 90 degrees to let the projected light reach the second reflecting surface 12 while the second reflecting surface 12 changes a direction of the reflected light from the first reflecting surface 11 at an angle of 90 degrees to let the reflected light reach the light-receiving part 102.

The inclined interface 13 is arranged to be permeated with the projected light from the light-emitting part 101 along the path P when the remaining ink is present and to reflect upward the projected light from the light-emitting part 101 out of the path P when the remaining ink is absent. In this case, the direction that the inclined interface 13 reflects the light when the remaining content is absent is set toward the inner side (the upper side) of the cartridge.

Other optically permeable surfaces 31, 32 and 33 are formed to be substantially orthogonal to a light-permeating direction. In Embodiment 1, a direction of the light permeating the permeable surfaces 31, 32 and 33 is a direction at a 90° angle with the emitting optical axis of the light-emitting part 101. Accordingly, the permeable surfaces 31, 32 and 33 are formed as a surface parallel to the emitting optical axis of the light-emitting part 101.

An operation of the apparatus for detecting the amount of remaining ink in Embodiment 1 will be described below.

First, the ink cartridge 1A is properly set in the cartridge setting part of the carriage 211, as shown in FIG. 1A. The light projected from the light-emitting part 101 reaches the light-receiving part 102 along the path P when the amount of the ink M remaining in the ink cartridge 1A is at a predetermined level or more.

That is to say, when the remaining ink is present (is at the predetermined level or more), the inclined interface 13 is soaked in the ink M having a refractive index almost equal to that of the inclined interface 13, so that the inclined interface 13 functions as a permeable surface to be permeated with the light projected from the light-emitting part 101. Accordingly, the light projected from the light-emitting part 101 is reflected on the first and second reflecting surfaces 11 and 12 to reach the light-receiving part 102.

Therefore, it can be judged that the ink cartridge 1A is loaded and the remaining ink M is present when the light-emitting part 101 emits light and the light-receiving part 102 receives the projected light.

On the other hand, as shown in FIG. 1B, the light projected from the light-emitting part 101 does not reach the light-receiving part 102 even in the case that the ink cartridge 1A is properly set when the amount of the remaining ink is less than the predetermined level.

That is to say, when the remaining ink is absent (less than the predetermined level), the inclined interface 13 is in contact with an atmosphere having a refractive index different from that of the inclined interface 13 to function as a reflecting surface, so that the light projected from the light-emitting part 101 is reflected in a direction out of the optical path P, which is in the case of presence of the ink. Accordingly, the light projected from the light-emitting part 101 does not reach the light-receiving part 102.

In the case that the ink cartridge 1A is not set in the cartridge setting part, as shown in FIG. 1C, the optical axes of the light-emitting part 101 and the light-receiving part 102 do not accord, so that the light projected from the light-emitting part 101 does not reach the light-receiving part 102 even when the light-emitting part 101 emits the light. Similarly to the above, the first and second reflecting surfaces 11 and 12 of the ink cartridge 1A do not effectively operate even when the remaining ink is present in the case that the ink cartridge 1A is not properly set in the cartridge setting part, for example. Accordingly, the light projected from the light-emitting part 101 does not reach the light-receiving part 102.

It is thus judged that, in the case that the light projected from the light-emitting part 101 does not reach the light-receiving part 102 even when the light-emitting part 101 emits the light, the ink cartridge 1A is not properly set or the remaining ink is absent in spite of proper setting. Accordingly, a light-receiving signal outputted from the light-receiving part 102 during emission of light from the light-emitting part 101 is judges to indicate a state that the ink is available (is present) while no light-receiving signal outputted from the light-receiving part 102 is judged to indicate a state that the ink is not available (absent).

That is to say, in accordance with the apparatus for detecting the amount of remaining ink in Embodiment 1, providing only one combination of the inclined interface 13 and the first and second reflecting surfaces 11 and 12 and once performing positioning between the light-emitting part 101 and the light-receiving part 102 and the ink cartridge 1A allow presence and/or absence of the ink cartridge 1A and presence and/or absence of the remaining ink to be judged at a time. This contributes to a simple structure and simplification of an operation for detection.

Further, the first and second two reflecting surfaces 11 and 12 are used to let the light projected from the light-emitting part 101 reach the adjacent light-receiving part 102. This allows the light-emitting part 101 and the light-receiving part 102 to be arranged on the same side, so that the light-receiving and light-emitting parts can be made compact, and thereby, the structure can be simplified.

Moreover, the reflecting direction of the inclined interface 13 is arranged to be toward the inner (upper) side of the cartridge in the case of absence of the remaining ink. This can prevent an error in operation such that the light projected from the light-emitting part 101 is reflected on another member on the outer (lower) side of the container to reach the light-receiving part 102.

<Embodiment 2>

Figure 4:
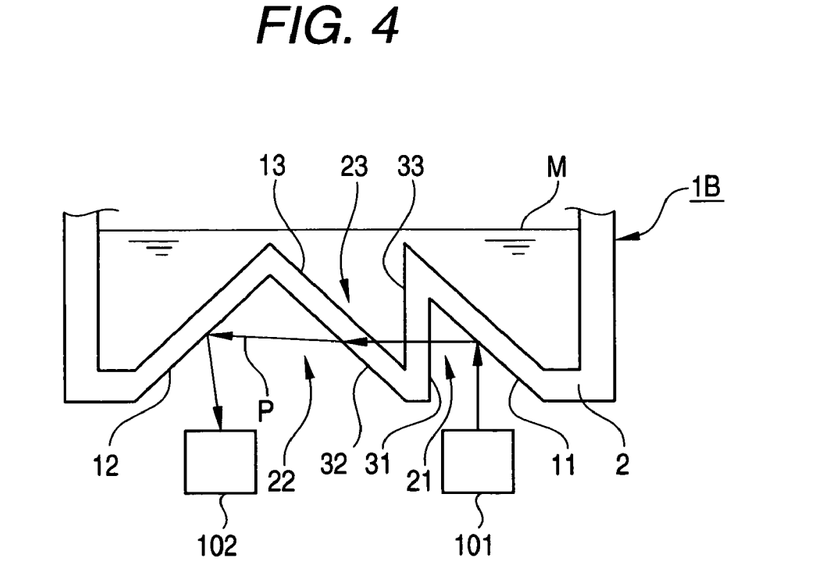
FIG. 4 is a schematically sectional view of a structure of an apparatus or detecting the amount of remaining ink in the second embodiment of the invention.

FIG. 4 is a schematically sectional view of a structure of an apparatus for detecting the amount of remaining ink in the second embodiment of the invention.

In an ink cartridge 1B of the apparatus for detecting the amount of remaining ink in Embodiment 2, a permeable surface (a wall surface of the container) 32 to be permeated with the light subsequently to the inclined interface 13, is formed to be parallel to the inclined interface 13 and the thickness of a wall part provided with the inclined interface 13 is made thin.

The permeable surface is preferably arranged vertically to the direction of permeation of light, originally, in order to avoid refraction of light in permeation of the permeable surface (in view of locational adjustment between the light-emitting part 101 and the light-receiving part 102). This, however, causes an unnecessary thick part, which is not preferable in the case of forming the ink cartridge from resin. Arrangement such as the ink cartridge 1B in Embodiment 2 prevents such a thick part from being formed. This causes refraction of permeating light, but adjusting a direction or a location of the light-emitting part 101, for example, can solve the refraction.

<Embodiment 3>

Figure 5:
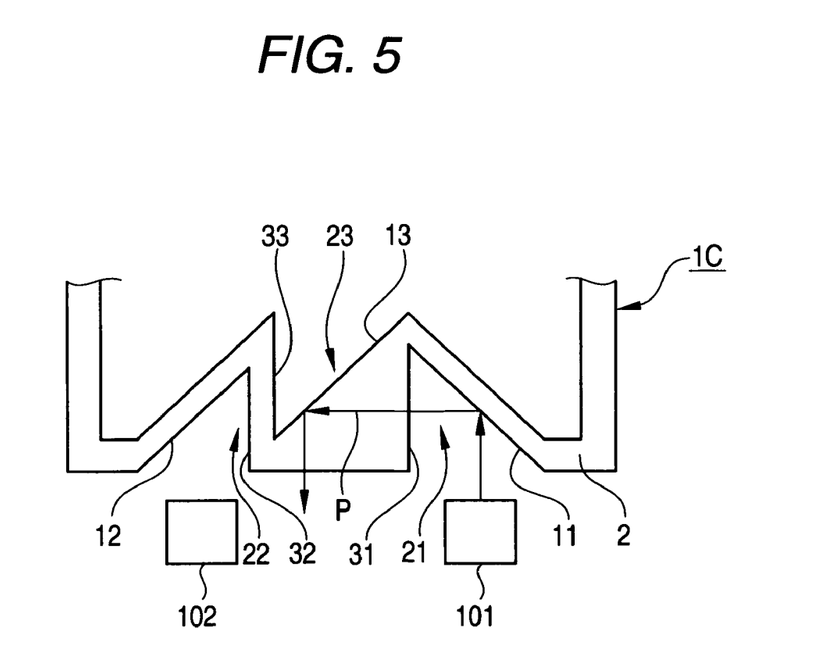
FIG. 5 is a schematically sectional view of a structure of an apparatus for detecting the amount of remaining ink in the third embodiment of the invention.

FIG. 5 is a schematically sectional view of a structure of an apparatus for detecting the amount of remaining ink in the third embodiment of the invention.

In an ink cartridge 1C of the apparatus for detecting the amount of remaining ink in Embodiment 3, the inclined interface 13 is provided with an angle oppositely to the inclined interface 13 in Embodiment 1. Such arrangement causes the direction of light reflected on the inclined interface 13 in the case of absence of the remaining ink to be toward the outer (lower) side of the cartridge. Accordingly, it is possible to prevent an error in operation such that the light projected from the light-emitting part 101 is reflected on an inner surface of a lid or the like on the inner (upper) side of the container to reach the light-receiving part 102.

<Embodiment 4>

Figure 6:
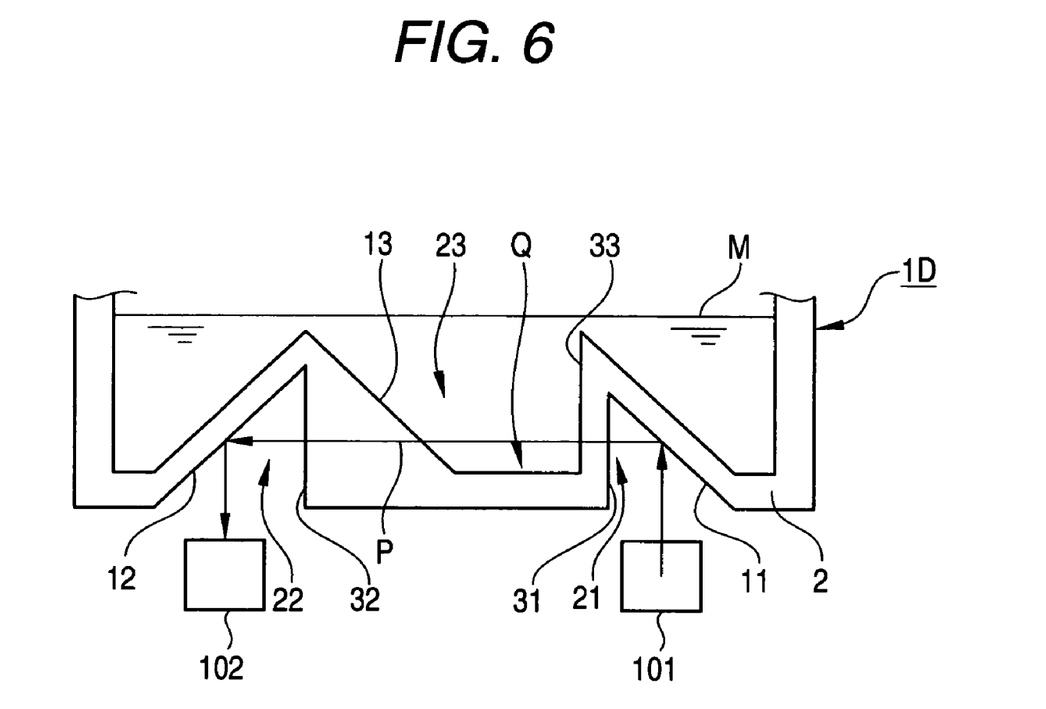
FIG. 6 is a schematically sectional view of a structure or an apparatus for detecting the amount of remaining ink in the fourth embodiment of the invention.

FIG. 6 is a schematically sectional view of a structure of an apparatus for detecting the amount of remaining ink in the fourth embodiment of the invention.

In an ink cartridge 1D of the apparatus for detecting the amount of remaining ink in Embodiment 3, a space Q for preventing wrong detection due to a meniscus of the ink M is secured on the inner side of the cartridge adjacently to the inclined interface 13. That is to say, a width of the concave 23, which is in the shape of a triangle in section in the ink cartridge 1A shown in FIG. 1, is enlarged so that the concave 23 would be in the shape of a trapezoid in section for the purpose of preventing the ink M from adhering due to a meniscus to the vicinity of a light incident part on the inclined interface 13.

In the case that the space adjacent to the inclined interface 13 is small like the ink cartridge 1A shown in FIG. 1, for example, the ink M adheres to the inclined interface 13 due to a meniscus operation in spite of little amount of the remaining ink M, so that the inclined interface 13 is likely not to function as a reflecting surface. This causes a probability of wrong detection.

Therefore, enlarging the space for reserving the ink M from the beginning to avoid influence of the meniscus allows the wrong detection due to the influence of the meniscus to be prevented.

<Embodiment 5>

Figure 7:
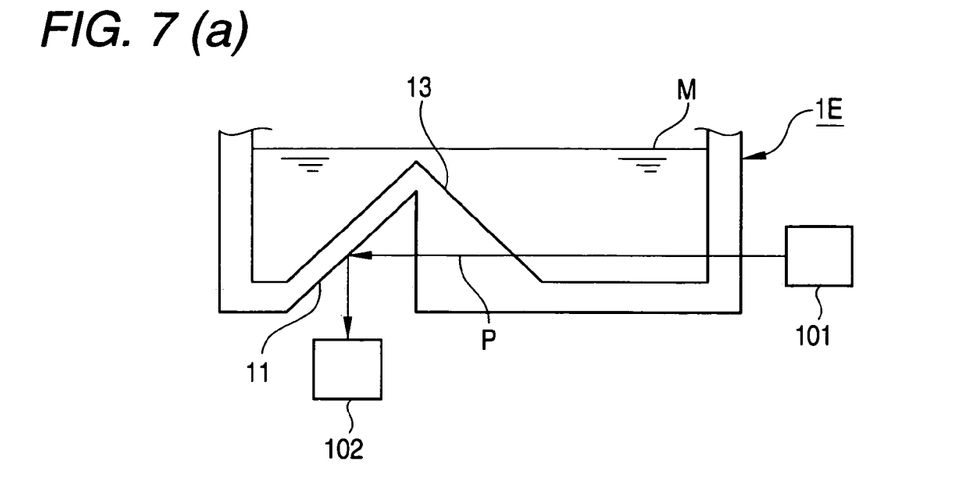

FIG. 7 is a schematically sectional view of a structure of an apparatus for detecting the amount of remaining ink in the fifth embodiment of the invention. FIG. 7A shows a condition that remaining ink is present in the apparatus. FIG. 7B shows a condition that the remaining ink is absent in the apparatus. FIG. 7C shows a condition that there is no cartridge in the apparatus.

In the apparatus for detecting the amount of remaining ink in Embodiment 5, the light-emitting part 101 and the light-receiving part 102 are arranged so as to have a relation that optical axes thereof would be orthogonal each other.

A reflecting surface of an ink cartridge 1E is only a first reflecting surface 11. The inclined interface 13 is provided in the path P along which the light projected from the light-emitting part 101 reaches the light-receiving part 102.

Accordingly, also in accordance with the apparatus for detecting the amount of remaining ink in Embodiment 5, providing only one combination of the inclined interface 13 and the first reflecting surface 11 and once performing positioning between the light-emitting part 101 and the light-receiving part 102 and the ink cartridge 1E allow presence and/or absence of the ink cartridge 1E and presence and/or absence of the remaining ink to be judged at a time. This contributes to a simple structure in addition to simplification of an operation for detection.

As described above, the light-emitting part 101 and the light-receiving part 102 may be in any arrangement so long as optical axes thereof do not accord each other and may be properly changed in shape so as to correspond to a shape in fitting in a main body of a printer. Further, a number or a location of the reflecting surface on the ink cartridge side does not matter as long as it is arranged that the reflecting surface can let the light projected from the light-emitting part 101 reach the light-receiving part 102 when the remaining ink is present.

FIG. 8 illustrates a whole structure of an ink-jet printer 200 on which the apparatus for detecting the amount of remaining ink in Embodiment 1 is mounted.

As shown in FIG. 8, the ink-jet printer 200 comprises a conveying roller 217 for conveying a sheet S and an ink-jet head 212 mounted on the carriage 211.

The carriage 211 is used as holding means for freely detachably holding the ink cartridge 1A. A timing belt 214, which is driven to rotate by a carriage driving motor (driving means) 213, reciprocates the carriage 211 in a direction of a width of the sheet along a guide shaft 215.

At a location out of a printing area, provided are detecting means 100 having the light-emitting part 101 and the light-receiving part 102 for radiating light and receiving reflected light to and from the first and second reflecting surfaces 11 and 12 and the inclined interface 13, which are provided in the ink cartridge 1A, for the purpose of detection of an amount of the remaining ink. The carriage 211 and the detecting means 100 are relatively moved by means of the carriage driving motor 213.

In detecting the amount of the remaining ink, the carriage 211 is moved to a position that the remaining amount detecting part 10A of the ink cartridge 1A faces the detecting means 100 so as to carry out detection.

A structure such as a container, a light-emitting part, a light-receiving part, a reflecting surface and an inclined interface of the content detecting apparatus in accordance with the invention is not limited to structures of the above-mentioned embodiments. It may be, of course, in various kinds of mode on the basis of the spirit of the invention.

In the above embodiments, exemplified is a case that the content is ink and the container is an ink cartridge, for example. The content detecting apparatus according to the invention, however, is applicable to a container, which houses liquid other than ink.

Further, a remaining content other than liquid can be detected as long as the content has a refractive index substantially equal to that of the container.

What is claimed is:

1. A content detecting apparatus for detecting presence and/or absence of a remaining content in a container by means of a signal from a light-receiving part receiving light projected from a light-emitting part, wherein the light-emitting part for projecting light toward the container set in a container setting part and the light-receiving part for receiving the light projected from the light-emitting part are arranged so that optical axes thereof would not accord, the container is provided with a reflecting surface for reflecting the light projected from the light-emitting part to let the projected light reach the light-receiving part when the remaining content is present and with an inclined interface, which is located in a path through which the light projected from the light-emitting part reaches the light-receiving part, for switching a function between permeation and reflection in accordance with presence and/or absence of the remaining content under a condition that the container is properly set in the container setting part, and the inclined interface permeates along the path with the light projected from the light-emitting part when the remaining content is present while the inclined interface reflects the light projected from the light-emitting part in a direction out of the path when the remaining content is absent.

2. The content detecting apparatus according to claim 1, wherein the reflecting surface includes a first reflecting surface for reflecting the light projected from the light-emitting part and a second reflecting part for reflecting the reflected light toward the light-receiving part and the inclined interface is provided between the first reflecting surface and the second reflecting surface.

3. The content detecting apparatus according to claim 1 or 2, wherein a direction of reflection of light by means of the inclined interface in the case of absence of the remaining content is set on the inner side of the container.

4. The content detecting apparatus according to claim 1 or 2, wherein a direction of reflection of light by means of the inclined interface in the case of absence of the remaining content is set on the outer side of the container.

5. The content detecting apparatus according to claim 1 or 2, wherein a container wall surface, which is permeated with light subsequently to the inclined interface, is formed parallel to the inclined interface.

6. The content detecting apparatus according to claim 1 or 2, wherein the content is liquid.

7. The content detecting apparatus according to claim 6, wherein a space for preventing wrong detection of the content due to a meniscus is secured in the inner side of the container adjacent to the inclined interface.

8. A container, which is loaded in a container setting part provided with a light-emitting part and a light-receiving part so that the optical axes of the light-emitting part and the light-receiving part would not accord and in which presence and/or absence of a remaining content is detected, the container comprising:

under a condition that the container is properly set in the container setting part, a reflecting surface for reflecting the light projected from the light-emitting part to let the projected light reach the light-receiving part when the remaining content is present; and an inclined interface, which is located in a path through which the light projected from the light-emitting part reaches the light-receiving part, for switching a function between permeation and reflection in accordance with presence and/or absence of the remaining content, the container wherein the inclined interface is arranged to be permeated along the path with the light projected from the light-emitting part when the remaining content is present and to reflect the light projected from the light-emitting part in a direction out of the path when the remaining content is absent.

9. The container according to claim 8, the container being in a mode of an ink cartridge capable of being loaded in an ink-jet printer, which houses ink as the content and uses the ink as a printing material.

10. An ink-jet printer comprising:

holding means for detachably holding a container, which is loaded in a container setting part provided with a light-emitting part and a light-receiving part so that the optical axes of the light-emitting part and the light-receiving part would not accord and in which presence and/or absence of a remaining content is detected, the container comprising;

under a condition that the container is properly set in the container setting part, a reflecting surface for reflecting the light projected from the light-emitting part to let the projected light reach the light-receiving part when the remaining content is present and an inclined interface, which is located in a path through which the light projected from the light-emitting part reaches the light-receiving part, for switching a function between permeation and reflection in accordance with presence and/or absence of the remaining content, the container, wherein the inclined interface is arranged to be permeated along the path with the light projected from the light-emitting part when the remaining content is present and to reflect the light projected from the light-emitting part in a direction out of the path when the remaining content is absent, and wherein the container is in a mode of an ink cartridge capable of being loaded in an ink-jet printer, which houses ink as the content and uses the ink as a printing material;

detecting means including the light-emitting part and the light-receiving part for radiating light and receiving reflected light to or from the reflecting surface and the inclined interface provided in the container; and driving means for relatively moving the holding means and the detecting means.

* * * * *